United States Patent
Villanova

(10) Patent No.: US 8,420,834 B2
(45) Date of Patent: Apr. 16, 2013

(54) PROCESS FOR MANUFACTURING ARTEMISININ

(75) Inventors: Luigi Villanova, Zollino (IT); Felicia Cisale, legal representative, Zollino (IT); Azzurra Villanova, legal representative, Zollino (IT); Luciano Villanova, legal representative, Zollino (IT)

(73) Assignee: Lachifarma S.r.l. Laboratorio Chimico Farmaceutico Salentino, Zollino (IT)

( * ) Notice: Subject to any disclaimer, the term of this patent is extended or adjusted under 35 U.S.C. 154(b) by 189 days.

(21) Appl. No.: 12/679,494

(22) PCT Filed: Sep. 25, 2008

(86) PCT No.: PCT/EP2008/008172
§ 371 (c)(1),
(2), (4) Date: May 7, 2010

(87) PCT Pub. No.: WO2009/040119
PCT Pub. Date: Apr. 2, 2009

(65) Prior Publication Data
US 2010/0331553 A1 Dec. 30, 2010

(30) Foreign Application Priority Data
Sep. 27, 2007 (IT) .............................. MI2007A1860

(51) Int. Cl.
*C07D 493/18* (2006.01)
*A61K 36/282* (2006.01)

(52) U.S. Cl.
USPC ............................ 549/279; 424/740; 424/774

(58) Field of Classification Search .......................... None
See application file for complete search history.

(56) References Cited

U.S. PATENT DOCUMENTS
6,180,105 B1 * 1/2001 Wheatley et al.

FOREIGN PATENT DOCUMENTS

| CN | 1 033 588 C | 12/1996 |
|---|---|---|
| CN | 1 935 810 A | 3/2007 |
| DE | 103 36 056 A1 | 2/2005 |
| FR | 2 706 166 A1 | 12/1994 |
| GB | 2 317 612 A | 4/1998 |

OTHER PUBLICATIONS

International Search Report, dated Jun. 12, 2009, from corresponding PCT application.
Tzu-Ching Tzeng et al., "Ethanol modified supercritical fluids extraction of scopoletin and artemisinin from *Artemisia annua* L.", Separation and Purification Technology, May 22, 2007, pp. 18-24, vol. 56, No. 1.
Marcel Kohler et al., "Extraction of artemisinin and artemisinic acid from *Artemisia annua* L. using supercritical carbon dioxide", Journal of Chromatography A, Oct. 17, 1997, pp. 353-360, vol. 785, Nos. 1-2.
Young-Lung Lin et al., "Supercritical Fluids Extraction of Artemisinin: Optimizing Recovery and Purity by Response Surface Methodology", World Congress of Chemical Engineering, Jul. 10, 2005, pp. 83320/1-83320/9.
Socrates Quispe-Condori et al., "Global yield isotherms and kinetic of artemisinin extraction from *Artemisia annua* L Leaves using supercritical carbon dioxide", The Journal of Supercritical Fluids, Nov. 1, 2005, pp. 40-48, vol. 36, No. 1.
He Chunmao et al, "Studies on extraction of Artemisinin from Sweet Wormwood (*Artemisia annua*) by Supercritical Carbon Dioxide", Zhongcaoyao—Chinese Traditional and Herbal Drugs, Jan. 1, 1999, pp. 497-499, vol. 30, No. 7.
Herman J. Woerdenbag et al., "Artemisinin, Related Sesquiterpenes, and Essential Oil in *Artemisia annua* During a Vegetation Period in Vietman", Planta Medica, Jun. 1, 1994, pp. 272-275, vol. 60, No. 3, XP-000881675.

* cited by examiner

*Primary Examiner* — Michele Flood
(74) *Attorney, Agent, or Firm* — Young & Thompson

(57) ABSTRACT

Disclosed is a process for manufacturing crude Artemisinin comprising the extraction of *Artemisia annua* from plant material with carbon dioxide or water in a critical physical state such that after extraction, the solvent evaporates completely from the resulting extract.

6 Claims, No Drawings

PROCESS FOR MANUFACTURING ARTEMISININ

FIELD OF INVENTION

The present invention relates to a process of extraction of Artemisinin from *Artemisia annua* and to the extract obtainable by said process.

BACKGROUND OF THE INVENTION

*Artemisia annua* has been used in China for centuries to treat malaria. Researchers from all over the world have demonstrated that preparations based on *Artemisia annua* are effective against malaria, even in its most acute forms, caused by infection by the parasite *Plasmodium falciparum*. The main chemical constituent of *Artemisia* responsible for this pharmacological activity has been identified as Artemisinin, a sesquiterpene structure containing an unusual peroxide bridge. The structure of Artemisinin is shown below:

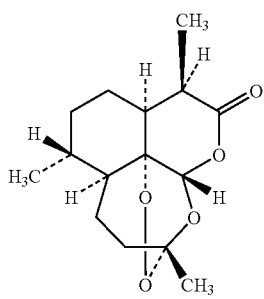 [SMILES: C[C@@H]1CC[C@H]2[C@@H](C)C(=O)O[C@@H]3O[C@@]4(C)CC[C@@H]1[C@]32OO4]

Clinical trials conducted with Artemisinin and semi-synthetic derivatives thereof such as Artesunate have confirmed its efficacy in the treatment of malaria. Artemisinin was recently synthesised, but the complexity of the molecule prevents its large-scale synthesis. This is confirmed by numerous research projects designed to synthesise Artemisinin analogues with a simpler structure. More recent studies have preferred to focus on *artemisia* extracts produced with non-polar organic solvents such as diethyl ether or, more commonly, petroleum ether.

However, the known processes do not enable a satisfactory Artemisinin content to be obtained. Moreover, it is very difficult to remove the traces of solvents to obtain a pharmaceutically acceptable product. The solvents are also used in large amounts in the known methods, and have therefore to be discarded or redistilled.

In recent years, carbon dioxide in the supercritical state has been used to isolate active pharmaceutical substances from plant materials. This technique has been used on an industrial scale for over 20 years to extract flavourings from herbs and spices. The carbon dioxide is removed rapidly and completely by depressurising the extraction apparatus, thus eliminating the problems associated with disposal of solvents and contamination of the finished product with traces of solvent. Moreover, the selectivity of supercritical carbon dioxide is generally greater than organic solvents of a polarity comparable to ethyl acetate or petroleum ether.

Similar procedures can also be successfully employed to extract active components from plant matrices using water in the subcritical state, either alone or mixed with other co-solvents.

DESCRIPTION OF THE INVENTION

It has now been found that crude Artemisinin can be advantageously obtained by extraction from the green parts of the *Artemisia annua* plant with carbon dioxide or water in the critical state, and their subsequent evaporation from the extract.

Another aspect of the invention provides an extract of *Artemisia annua* containing approx. 3% by weight of Artemisinin substantially free from traces of residual organic solvents.

Co-eluents, namely small amounts of solvents which can modify the polarity of the mixture, can also be used at the extraction step. For example, methyl alcohol, ethyl alcohol, acetonitrile, ethyl acetate, petroleum ether, n-hexane, and preferably ethanol can be used for that purpose, in order to obtain pharmaceutical grade Artemisinin. Said co-eluents can be used in amounts ranging between 0.5 and 30%, usually 5% by weight.

The process according to the invention provides an extract with a high Artemisinin content and no trace of organic solvents.

The process according to the invention is preferably performed at an extraction pressure between 0.5 and 100 MPa, usually under a pressure of 50 MPa, and a temperature range between 20 and 150° C. (usually 70-80° C.), with the use of carbon dioxide and/or water in the critical state, with or without the use of co-eluents.

The invention is disclosed in greater detail in the example below.

EXAMPLE

Dried parts of leaves of the plant *Artemisia annua* were packed into a vessel resistant to pressure. A volume of liquid carbon dioxide, in the ratio of approx. 4:1 of anhydride in the critical state to 100 g of plant material, was forced through the crude material at the speed of approx. 20 rpm. The liquid carbon dioxide was thus collected, and the pressure reduced and balanced with atmospheric pressure to allow the anhydride to be dispersed in the atmosphere. The residue extracted and collected from the extraction chamber presented as an oil or semi-solid, depending on the exact extraction conditions.

With carbon dioxide, the following extraction conditions were used:

| Extraction pressure | Extraction temperature | Speed | Sample | Artemisinin |
|---|---|---|---|---|
| 10 MPa | 80° C. | 20 g min$^{-1}$ | 100 g | 0.07% |
| 20 MPa | 80° C. | 20 g min$^{-1}$ | 100 g | 0.9% |
| 30 MPa | 80° C. | 20 g min$^{-1}$ | 100 g | 1.8% |
| 50 MPa | 80° C. | 20 g min$^{-1}$ | 100 g | 3.1% |
| 70 MPa | 80° C. | 20 g min$^{-1}$ | 100 g | 2.9% |

The Artemisinin content was determined by liquid chromatography coupled with mass spectrometry (LC/MS).

The use of carbon dioxide without the addition of co-elution solvents gives good results: the Artemisinin content obtained from the extract is approx. 3%.

Other extraction conditions yield a lower Artemisinin content.

As an alternative to the use of carbon dioxide, water in the subcritical state can be employed, and already provides good results without the addition of co-elution solvents.

Dried parts of leaves of the plant *Artemisia annua* were packed into a vessel resistant to pressure. A volume of steam, in the ratio of approx. 5:1 of water in the critical state to 100 g of plant material, was forced through the crude material at the rate of approx. 15 ml/10 min. The steam was collected, and the pressure was reduced and balanced with atmospheric pressure to allow the steam to disperse in the atmosphere. The residue extracted and collected from the extraction chamber always presented as an oil or semi-solid, depending on the exact extraction conditions.

With water, the following extraction conditions were used:

| Extraction pressure | Extraction temperature | Speed | Sample | Artemisinin |
|---|---|---|---|---|
| 1 MPa | 125° C. | 15 ml min$^{-1}$ | 100 g | 1.6% |
| 2 MPa | 125° C. | 15 ml min$^{-1}$ | 100 g | 2.3% |
| 5 MPa | 125° C. | 15 ml min$^{-1}$ | 100 g | 2.8% |
| 10 MPa | 125° C. | 15 ml min$^{-1}$ | 100 g | 0.7% |
| 20 MPa | 125° C. | 15 ml min$^{-1}$ | 100 g | 0.09% |

The Artemisinin content was determined by liquid chromatography coupled with mass spectrometry (LC/MS).

For the purpose of direct comparison, the Artemisinin content extracted from the same plant material with conventional solvents such as n-hexane and ethyl acetate only amounted to 0.6%, determined in the same way as for LC/MS.

The Artemisinin content in the crude material used, extracted by the conventional method for organic solvent, agrees with the findings published in the literature, namely an interval ranging between 0.01 and 0.6% w/w for *Artemisia annua* extracted with conventional solvents.

The invention claimed is:

1. A process for manufacturing artemisinin, comprising extracting *Artemisia annua* plant material with water under a pressure of between 0.5 MPa and 100 MPa and at a temperature of between 20° C. and 150° C.; and evaporating the water to obtain an extract comprising the artemisinin.

2. The process as claimed in claim 1, wherein the extract comprises 0.09-2.8% (w/w) of artemisinin.

3. The process as claimed in claim 1, wherein the pressure is 1-20 MPa.

4. The process as claimed in claim 1, wherein the temperature is 125° C.

5. The process as claimed in claim 1, wherein the extract comprises 2.8% (w/w) of artemisinin.

6. The process as claimed in claim 1, wherein the temperature is 70-80° C.

* * * * *

UNITED STATES PATENT AND TRADEMARK OFFICE
CERTIFICATE OF CORRECTION

PATENT NO.       : 8,420,834 B2
APPLICATION NO.  : 12/679494
DATED            : April 16, 2013
INVENTOR(S)      : Luigi Villanova It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 277 days.

Signed and Sealed this
Eighth Day of September, 2015

Michelle K. Lee
*Director of the United States Patent and Trademark Office*